United States Patent [19]

Henke et al.

[11] Patent Number: 5,206,343

[45] Date of Patent: Apr. 27, 1993

[54] OLIGOPEPTIDES WITH CYCLIC PROLINE-ANALOGOUS AMINO ACIDS

[75] Inventors: Stephan Henke, Bad Soden am Taunus; Dietrich Brocks, Wiesbaden; Volkmar Günzlen-Pukall, Marburg-Cappel, all of Fed. Rep. of Germany; Kari I. Kivirikko; Raili M. H. Myllylä, both of Oulu, Finland

[73] Assignee: Hoechst Aktiengesellschaft, Frankfurt am Main, Fed. Rep. of Germany

[21] Appl. No.: 360,177

[22] Filed: Jun. 1, 1989

[51] Int. Cl.$^5$ .................... A61K 37/02; C07D 231/00
[52] U.S. Cl. .................... 530/331; 548/356.1; 930/20
[58] Field of Search .............. 514/18, 403; 530/331, 530/330; 930/20; 548/356

[56] References Cited

U.S. PATENT DOCUMENTS

| | | | |
|---|---|---|---|
| 4,425,333 | 1/1984 | Iwao et al. | 424/177 |
| 4,761,399 | 8/1988 | Pilotto et al. | 514/19 |
| 4,840,936 | 6/1989 | Della Bella et al. | 514/18 |
| 4,952,596 | 8/1990 | Della Bella et al. | 514/365 |
| 4,971,993 | 11/1990 | Kurauchi et al. | 514/422 |

FOREIGN PATENT DOCUMENTS

| | | |
|---|---|---|
| 190852 | 1/1986 | European Pat. Off. |
| 254354 | 7/1987 | European Pat. Off. |
| 271865 | 12/1987 | European Pat. Off. |
| 322068 | 12/1988 | European Pat. Off. |
| WO81/02893 | 10/1981 | PCT Int'l Appl. |
| WO86/02353 | 4/1986 | PCT Int'l Appl. |

OTHER PUBLICATIONS

Fairweather, R., and Jones, J. H., J Chem. Soc. Perkins I, 1972, pp. 2475-2481.
Gunzler, V. et al., J Biol. Chem. 263, pp. 19498-19504 (1988).

Primary Examiner—Merrell C. Cashion, Jr.
Assistant Examiner—Bennett Celsa
Attorney, Agent, or Firm—Finnegan, Henderson, Farabow, Garrett & Dunner

[57] ABSTRACT

The invention relates to compounds of the formula I

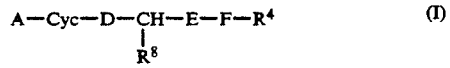

in which A denotes an optionally substituted radical from the series comprising alkyl, acyl, cycloalkyl, aryl and heteroaryl; Cyc represents an optionally substituted heterocyclic carbonyl compound; D represents NH, NCH$_3$, O or CH$_2$; E represents CHOH, CO, SO or optionally N-substituted C=NH; F represents O, NH, NCH$_3$ or a bond; R$^4$ denotes an optionally substituted radical from the series comprising alkyl, cycloalkyl, aryl and heteroaryl; and R$^8$ denotes hydrogen or optionally substituted alkyl, to a process for the preparation thereof, and to the use thereof as inhibitors of prolyl hydroxylase.

3 Claims, No Drawings

OLIGOPEPTIDES WITH CYCLIC PROLINE-ANALOGOUS AMINO ACIDS

DESCRIPTION

The invention relates to oligopeptides with cyclic unnatural amino acids, which are effective inhibitors of prolyl hydroxylase.

2,3-Disubstituted isoxazolidines and the use thereof as inhibitors of prolyl hydroxylase are described in German Patent Application No. 3,643,012.9.

The invention has the object of finding new effective inhibitors of prolyl hydroxylase whose proline residue is replaced by cyclic unnatural amino acids.

This object is achieved by the compounds of the formula I

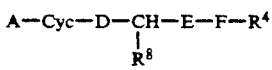

in which

A
- $a_1$) denotes $(C_1-C_8)$-alkyl,
  $(C_1-C_8)$-alkanoyl,
  $(C_1-C_8)$-alkoxycarbonyl or
  $(C_1-C_8)$-alkylsulfonyl, in which in each case 1, 2 or 3 hydrogen atoms are optionally replaced by 1, 2 or 3 identical or different radicals from the series comprising carboxyl, amino, $(C_1-C_4)$-alkylamino, hydroxyl, $(C_1-C_4)$-alkoxy, halogen, di-$(C_1-C_4)$-alkylamino, carbamoyl, sulfamoyl, $(C_1-C_4)$-alkoxycarbonyl, $(C_6-C_{12})$-aryl and $(C_6-C_{12})$-aryl-$(C_1-C_5)$-alkyl, or in which in each case 1 hydrogen atom is optionally replaced by a radical from the series comprising $(C_3-C_8)$-cycloalkyl. $(C_1-C_4)$-alkylsulfonyl, $(C_1-C_4)$-alkylsulfinyl, $(C_6-C_{12})$-aryl-$(C_1-C_4)$-alkylsulfonyl $(C_6-C_{12})$-aryl-$(C_1-C_4)$-alkylsulfinyl $(C_6-C_{12})$-aryloxy, $(C_3-C_9)$-heteroaryl and $(C_3-C_9)$-heteroaryloxy and 1 or 2 hydrogen atoms are replaced by 1 or 2 identical or different radicals from the series comprising carboxyl, amino, $(C_1-C_4)$-alkylamino, hydroxyl, $(C_1-C_4)$-alkoxy, halogen, di-$(C_1-C_4)$-alkylamino, carbamoyl, sulfamoyl, $(C_1-C_4)$-alkoxycarbonyl, $(C_6-C_{12})$-aryl and $(C_6-C_{12})$-aryl-$(C_1-C_5)$-alkyl,
- $a_2$) denotes $(C_3-C_8)$-cycloalkyl,
  $(C_6-C_{12})$-aryl,
  $(C_6-C_{12})$-arylsulfonyl or $(C_3-C_9)$-heteroaryl, where, in the radicals defined under $a_1$) and $a_2$), in each case $(C_6-C_{12})$-aryl or $(C_3-C_9)$-heteroaryl is optionally substituted by 1, 2 or 3 identical or different radicals from the series comprising
  carboxyl,
  amino,
  nitro,
  $(C_1-C_4)$-alkylamino,
  hydroxyl,
  $(C_1-C_4)$-alkoxy,
  halogen,
  cyano,
  di-$(C_1-C_4)$-alkylamino,
  carbamoyl,
  sulfamoyl and
  $(C_1-C_4)$-alkoxycarbonyl,
  or
- $a_3$) denotes a radical of the formula IIa or IIb

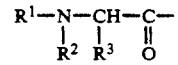

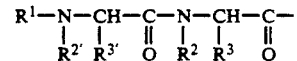

$R^1$
- $b_1$) denotes hydrogen or
- $b_2$) is defined as A under $a_1$) or $a_2$),
- $c_1$) $R^2$ and $R^{2'}$ are identical or different and denote hydrogen or methyl,
  $R^3$ and $R^{3'}$ are identical or different and denote hydrogen or $(C_1-C_6)$-alkyl, preferably $(C_1-C_4)$-alkyl, which is optionally monosubstituted by
  amino,
  benzyloxycarbonylamino,
  hydroxyl,
  carboxyl,
  carbamoyl,
  guanidino,
  ureido,
  mercapto,
  methylmercapto,
  phenyl,
  4-chlorophenyl,
  4-fluorophenyl,
  2-nitrophenyl,
  4-methoxyphenyl,
  4-hydroxyphenyl,
  phthalimido,
  4-imidazolyl,
  3-indolyl,
  2-thienyl,
  3-thienyl,
  2-pyridyl,
  3-pyridyl, or
  cyclohexyl,
- $c_2$) $R^2$ and $R^3$ and/or $R^{2'}$ and $R^{3'}$ in each case together represent a [—$CH_2$—$CH_2$—$C_2$—] chain in which one $CH_2$ group can be replaced by O, or
- $c_3$) $R^2$ and $R^3$ and/or $R^{2'}$ and $R^{3'}$ in each case together represent

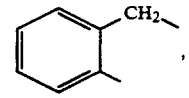

Cyc corresponds to one of the following heterocyclic rings, such as

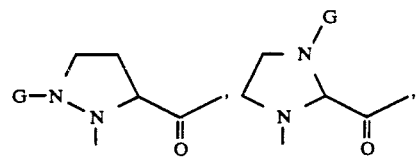

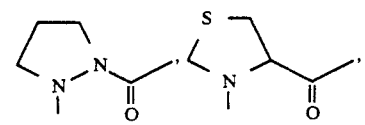

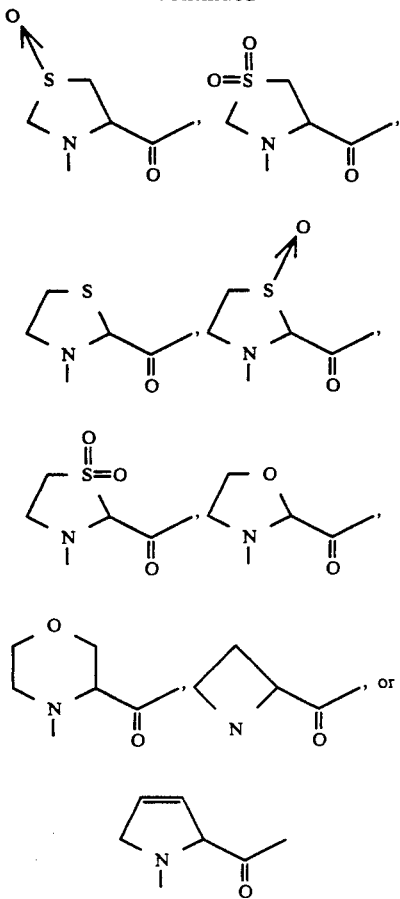

where G denotes hydrogen or is defined as A under a₁) or a₂),

D denotes
 imino,
 N-methylimino,
 oxy or
 methylene,

E denotes
 carbonyl,
 C=NR⁷,
 C=N—OR⁷ or
 sulfinyl, or can also denote hydroxymethylene if F represents a bond, R⁷ denotes
 hydrogen,
 $(C_1-C_8)$-alkyl, or
 $(C_3-C_8)$-cycloalkyl, F denotes
 oxy,
 imino,
 N-methylimino or
 a direct bond, R⁴ denotes
 $(C_1-C_6)$-alkyl,
 $(C_3-C_6)$-cycloalkyl,
 $(C_6-C_{12})$-aryl,
 $(C_6-C_{12})$-aryl-$(C_1-C_5)$-alkyl,
 $(C_6-C_{12})$-aryloxy-$(C_1-C_5)$-alkyl,
 $(C_3-C_9)$-heteroaryl or $(C_3-C_9)$-heteroaryl-$(C_1-C_5)$-alkyl, in which in each case alkyl is optionally substituted by 1 or 2 identical or different radicals from the series comprising
 carboxyl,
 amino,
 $(C_1-C_4)$-alkylamino,
 hydroxyl,
 $(C_1-C_4)$-alkoxy,
 halogen,
 di-$(C_1-C_4)$-alkylamino,
 carbamoyl,
 sulfamoyl,
 $(C_1-C_4)$-alkoxycarbonyl,
 $(C_6-C_{12})$-aryl and
 $(C_6-C_{12})$-aryl-$(C_1-C_5)$-alkyl, and in which in each case $(C_6-C_{12})$-aryl or $(C_3-C_9)$-heteroaryl is optionally substituted by 1, 2 or 3 identical or different radicals from the series comprising
 carboxyl,
 cyano,
 amino,
 nitro,
 $(C_1-C_4)$-alkylamino,
 hydroxyl,
 $(C_1-C_4)$-alkoxyl,
 halogen,
 di-$(C_1-C_4)$-alkylamino,
 carbamoyl,
 sulfamoyl and
 $(C_1-C_4)$-alkoxycarbonyl, and R⁸ is defined as R³ under c₁), as well as the physiologically tolerated salts thereof.

$(C_6-C_{12})$-aryl means, for example, phenyl, naphthyl or biphenylyl. A corresponding statement applies to radicals derived therefrom, such as aroyl.

Alkyl and radicals derived therefrom, such as alkoxy, can be straight-chained or branched.

Halogen preferably represents fluorine, chlorine or bromine.

A heteroaryl radical within the meaning of the present invention is the radical of a monocyclic or bicyclic $(C_3-C_9)$-heteroaromatic compound which contains one or two nitrogen atoms and/or one sulfur or oxygen atom in the ring system. Regarding the term "heteroaromatic compound", see Garatt, Vollhardt, Aromatizität (Aromaticity), Stuttgart 1973, pages 131-153. Examples of suitable heteroaryl radicals are the radicals of thiophene, furan, benzo[b]thiophene, benzofuran, pyrrole, imidazole, pyrazole, pyridine, pyrazine, pyrimidine, pyridazine, indole, quinoline, isoquinoline, oxazole, isoxazole, isoindole, indazole, phthalazine, naphthyridine, quinoxaline, quinazoline, cinnoline and furazan. Aryl, alkyl, heteroaryl and radicals derived therefrom can be substituted once or, if chemically possible, also more than once, as indicated above.

Unless otherwise indicated, centers of chirality can e in the R or in the S configuration. The invention relates to the optically pure compounds as well as to mixtures of stereoisomers such as mixtures of enantiomers and mixtures of diastereomers.

Suitable salts are, in particular, alkali metal and alkaline earth metal salts, salts with physiologically tolerated amines and salts with inorganic or organic acids such as, for example, HCl, HBr, $H_2SO_4$, maleic acid and fumaric acid.

Preferred compounds of the formula I are those in which A denotes optionally substituted $(C_1-C_8)$-alkyl, $(C_1-C_8)$-alkanoyl or optionally substituted $(C_1-C_8)$-alkoxycarbonyl, or is defined as above under a3), those in which $R^8$ denotes hydrogen, and hose in which Cyc denotes

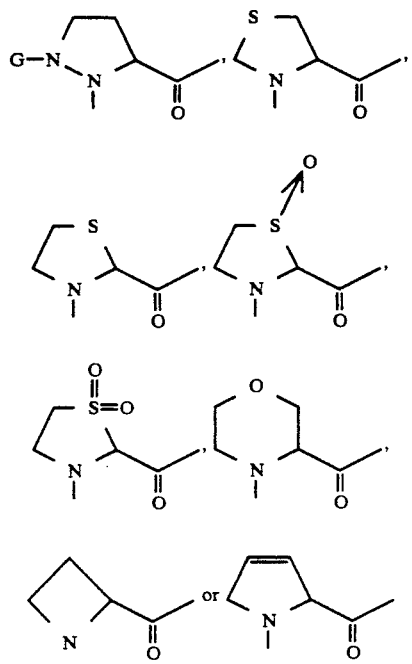

in which G represents hydrogen or is defined as A under a1) or a2).

Additional preferred compounds of the formula I are those in which D denotes imino, oxy or methylene, particularly preferably imino, E denotes carbonyl, F denotes oxy or a direct bond, and/or $R^4$ denotes optionally substituted $(C_6-C_{12})$-aryl, or $(C_6-C_{12}\text{-aryl-}C_1-C_5)$-alkyl which is optionally substituted in the alkyl moiety and/or optionally substituted in the aryl moiety, with suitable substituents of the aryl moiety being, in particular, halogens, pseudohalogens and carboxy groups, and suitable substituents of the alkyl moiety being, in particular, carboxyl, $(C_1-C_4)$-alkoxycarbonyl and amino groups.

Particularly preferred compounds of the formula I are those in which A represents substituted $(C_1-C_8)$-alkanoyl, examples of suitable substituents being $(C_6-C_{12})$-aryl-$(C_1-C_4)$-alkylsulfonyl and $(C_6-C_{12})$-aryl-$(C_1-C_4)$-alkylsulfinyl, or represents a radical of the formula IIa as defined above under a3).

The invention also relates to a process for the preparation of compounds of the formula I, which comprises building up the compounds in a known manner from the fragments, for example by coupling thereof, where appropriate eliminating one or more temporarily introduced protective group(s), converting carbonyl groups into the thia analogs where appropriate, and converting the compounds of the formula I which have been obtained in this way into the physiologically tolerated salts thereof where appropriate.

In the above sense, fragments mean amino acids, segments containing several amino acids, and derivatives of of amino acids, derivatives of peptides with modified peptide linkages, as well as carboxylic acids substituted in a variety of ways, various alcohols and the derivatives thereof.

The coupling can be carried out, for example, by condensing, in an inert solvent, a fragment of a compound of the formula I with a terminal carboxyl group, or with a reactive acid derivative, with another corresponding fragment which contains, for example, a free amino group, it being possible for any functional groups which are present and not involved in the reaction to be protected where appropriate, with the formation of an amide linkage. Methods suitable for forming an amide linkage are described in Houben-Weyl, Methoden der organischen Chemie (Method of Organic Chemistry), volume 15/12.

The process is advantageously carried out in such a manner that
a) a compound of the formula IIIa is condensed with a compound of the formula IIIb $$A-X \qquad \text{(IIIa)}$$

$$H-Cyc-D-CH-E-F-R^4 \qquad \text{(IIIb)}$$
$$\qquad\qquad\quad|$$
$$\qquad\qquad\;R^8$$

in which A, Cyc, D, E, F, $R^4$ and $R^8$ are as defined above, and X represents a nucleophilically detachable leaving group such as OH, Cl, Br, I, tosyl, triflate or, if A is an acyl radical, also represents an active ester group,
b) a compound of the formula IVa is condensed with a compound of the formula IVb $$A-Cyc-X \qquad \text{(IVa)}$$

$$H-D-CH-E-F-R^4 \qquad \text{(IVb)}$$
$$\qquad\;|$$
$$\qquad R^8$$

in which A, Cyc, E, F, $R^4$ and $R^8$ are as defined above, D represents imino, N-methylimino or oxy, and X represents a nucleophilically detachable leaving group such as OH, Cl, Br, I, tosyl, triflate or an active ester group, or
c) a compound of the formula Va is condensed with a compound of the formula Vb $$A-Cyc-D-CH-E-X \qquad \text{(Va)}$$
$$\qquad\qquad\;|$$
$$\qquad\qquad R^8$$

$$H-F-R^4 \qquad \text{(Vb)}$$

in which A, Cyc, D, $R^4$ and $R^8$ are as defined above, E is as defined above with the exception of hydroxymethylene, F denotes oxy, imino or N-methylimino, and X represents a nucleophilically detachable leaving group such as OH, Cl, Br, I, tosyl, triflate or an active ester group.

The reaction of a carboxylic acid of the formula IIIa, IVa or Va with the appropriate compound of the formula IIb, IVb or Vb with a free amino group is preferably carried out in a solvent customary in peptide chemistry, or else in water/solvent mixtures, in the presence of a suitable condensing agent such as, for example,
1. dicylcohexylcarbodiimide with the addition of 1-hydroxybenzotriazole (DCC/HOBt method, Lit.: Chem. Ber. 103 (1970) 788)

2. dicyclohexylcarbodiimide with the addition of 3-hydroxy-4-oxo-3,4-dihydro-1,2,3-benzotriazine (CDD/HOOBt method: Lit.: Chem. Ber. 103 (1970) 2034)
3. dicyclohexylcarbodiimide with the addition of N-hydroxysuccinimide (DCC/HONSu method; Lit.: Z. Naturforsch. 21b (1966) 426)
4. alkanephosphonic anhydride such as n-propylphosphonic anhydride (PPA method; Lit.: Angew. Chemie. Int. Ed. 19 (1980) 133)
5. dialkylphosphinic anhydride such as methylethylphosphinic anhydride (MEPA method; Lit.: U.S. Pat. No. 4,426,325).

Solvents suitable for use in the process according to the invention are, for reasons of solubility, usually polar solvents such as, for example, dimethylacetamide, dimethylformamide, dimethyl sulfoxide, phosphoric tris-(dimethylamide), N-methylpyrrolidone, water or mixtures of the said solvents with water. The latter applies in particular to the MEPA process. However, chloroform, methylene chloride or ethyl acetate are also employed. The synthesis can be carried out between $-10°$ and about 50° C., preferably $-10°$ C. and room temperature. It is preferably started at about 0° C. and subsequently raised to room temperature.

The condensation of a carboxylic acid of the formula IVa or VA with an alcohol of the formula IVb or Vb to give a carboxylic ester can advantageously be carried out by the dicyclohexylcarbodiimide (CDD) method, as described in Angew. Chem. 90, 556 (1978), in an inert solvent such as DMF with catalysis by 4-dimethylaminopyridine in the temperature range between $-20°$ to $+40°$ C., preferably $-20°$ C. to room temperature.

Methods suitable for the preparation of a modified peptide linkage are described in Janssen Chimica Acta, Vol. 3, No. 2 [1985]. The following methods are preferably employed:

synthesis of derivatives with reduced peptide linkages by reductive amination of aldehydes with amino acid esters using sodium cyanoborohydride (cf. Borch et al., J. Amer. Chem. Soc. 93 [1971] 2897; 91 [1969] 3996) or by N-alkylation of amines or amino acid derivatives (cf. Houben-Weyl, Methoden der Org. Chemie, vol. 11/1), by d) reacting a compound of the formula VIa, VIb or VIc with a compound of the formula IIIb

  A'—CHO  (VIa)

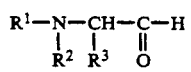 (VIb)

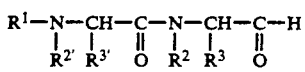 (VIc)

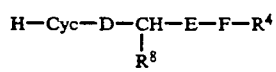 (IIIb)

in which Cyc, D, E, F, $R^1$, $R^2$, $R^{2'}$, $R^3$, $R^{3'}$, $R^4$ and $R^8$ are as defined above, and A $\alpha$ represents $(C_1-C_8)$-alkyl which is optionally substituted as A under $a_1$), or represents $(C_3-C_8)$-cycloalkyl, $(C_6-C_{12})$-aryl or $(C_3-C_9)$-heteroaryl, which are optionally substituted as A under $a_2$), e) reacting a compound of the formula VIIa with a compound of the formula VIIb

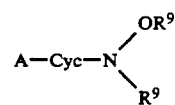 (VIIa)

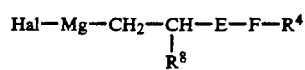 (VIIb)

in which A, E, F, Cyc, $R^4$ and $R^8$ are as defined above, $R^9$ denotes $(C_1-C_6)$-alkyl, preferably methyl, and Hal denotes chlorine, bromine or iodine. The reaction is preferably carried out in an ether such as diethyl ether, dibutyl ether, diisoamyl ether or tetrahydrofuran at a temperature between $-80°$ C. and the boiling point of the reaction mixture. Functional groups should, if necessary, be temporarily protected with protective groups which are stable to organometallic reagents.

Endothiopeptides are advantageously obtained by reaction of the compounds of the general type I with Lawesson's reagent (2,4-bis(4-methoxyphenyl)-1,3-dithia-2,4-diphosphetane 2,4-disulfide) (cf. Synthesis 1979, 941).

Protective groups suitable for the temporary protection of other functional groups are those customarily used in peptide synthesis and described, for example, in Kontakte Merck 3/79, pages 14-22 and 1/80, pages 23-35.

Examples of urethane protective groups of the amino group are Pyoc, Fmoc, Fcboc, Z, Boc, Ddz, Bpoc, Z-($NO_2$), Dobz, Moc, Mboc, Iboc, Adoc, Adpoc, Msc or Pioc; Z or Boc are preferred. These amino protective groups are removed by acids, bases or reduction.

Examples of protective groups of the guanidino group are $NO_2$, tosyl, Boc, Z, mesitylene-2-sulfonyl (Mts) and the like. Elimination can be effected by hydrolysis or hydrogenolysis.

The COOH side groups are blocked as alkyl esters, preferably methyl, ethyl or tert.butyl esters or as benzyl esters or modified benzyl esters (p-$NO_2$, p-Cl, p-Br inter alia). The deblocking is effected by alkaline or acid hydrolysis or hydrogenation.

Examples of hydroxyl protective groups are tert.butyl or benzyl.

The substances according to the invention are effective as inhibitors of prolyl hydroxylase. As a consequence, they bring about a selective inhibition of the collagen-specific hydroxylation reaction during the course of which protein-bound proline is hydroxylated by the enzyme prolyl hydroxylase. Suppression of this reaction by an inhibitor results in an underhydroxylated collagen molecule which is incapable of functioning and can be released from the cell into the extracellular space only in small amounts. In addition, the underhydroxylated collagen cannot be incorporated in the collagen matrix and very readily undergoes proteolytic degradation. The conscience of these effects is an overall reduction in the amount of collagen undergoing extracellular deposition. Inhibitors of prolyl hydroxylase are therefore suitable tools in the therapy of diseases in which the deposition of collagens makes a crucial contribution to the clinical picture. These include, inter alia, fibroses of the lungs, liver and skin (scleroderma) as well as atherosclerosis.

It is furthermore known that inhibitors of collagen production have antitumor properties. The reduction in collagen synthesis and deposition influences the stroma transformation necessary for tumor growth (H. Dvorak, N. Engl, J. of Med. 315 (1986) 1650); and inhibitors of basement membrane formation are suitable for suppressing the growth of various tumors (W. Klohs et al., J. N. C. I. 75 (1985) 353).

In addition, it is known that inhibition of prolyl hydroxylase by known inhibitors such as α,α-dipyridyl results in inhibition of Clq biosynthesis by macrophages (W. Müller et al., FEBS Lett. 90, 218f, (1978)). This results in the classical pathway of complement activation becoming inoperative. Inhibitors of prolyl hydroxylase thus also act as immunosuppressants, for example in immune complex diseases.

The substances according to the invention can therefore be used as fibrosuppressants, immunosuppressants, anti-atherosclerotics and in tumor therapy.

The inhibitory action can be determined in an enzyme assay in analogy to the method of B. Peterkofsky and R. DiBlasio, Anal. Biochem. 66, 279-286 (1975). This entails underhydroxylated collagen being enzymatically hydroxylated with prolyl hyroxylase in the presence of iron(II) ions, α-ketoglutarate and ascorbate.

To determine an irreversible type of inhibition, the enzyme is preincubated in the presence of iron(II) ions, α-ketoglutarate and ascorbate with the inhibitors for various times and subsequently the remaining activity of the enzyme is determined in the presence of peptide substrate. It is possible to employ for activity determination the method of Peterkofsky and DiBlasio described above as well as other methods such as described by K. I. Kivirikko and R. Myllylä, Meth. Enzym. 82, 245-304 (1982).

The inhibitory action can also be determined in cell or tissue culture. It is possible to employ for this fibroblasts or other collagen-producing cells or calvariae or other collagen-producing organs. The action of the substances can be determined via the reduction in the hydroxyproline/proline quotient on feeding with $^{14}$C-proline.

The anitfibrotic action can be determined in the model of liver fibrosis induced by carbon tetrachloride. For this, rats are treated twice a week with $CCl_4$ (1 ml/kg) dissolved in olive oil. The test substance is administered each day, where appropriate twice a day, orally or intraperitoneally, dissolved in a suitable tolerated solvent. The extent of liver fibrosis is determined histologically; the proportion of collagen in the liver is analyzed by determination of hydroxyproline as described by Kivirikko et al. (Anal. Biochem. 19, 249 et seq., (1967)). The fibrogenesis activity can be determined by radioimmunological determination of collagen fragments and procollagen peptides in the serum. The compounds according to the invention are effective in concentrations of 1-100 mg/kg in this model. Another model for evaluating the anitfibrotic action is that of bleomycin-induced lung fibrosis as described by Kelley et al. (J. Lab. Clin. Med. 96, 954 (1980)). To evaluate the action of the compounds according to the invention on granulation tissue it is possible to employ the cotton pellet granuloma model as described by Meier et al., Experientia 6, 469 (1950).

The invention therefore relates to the use of a compound of the formula I as inhibitor of prolyl hydroxylase as well as to the use thereof as a medicine in mammals and in humans, especially as fibrosuppressants, immunosuppressants, antiatherosclerotics and in tumor therapy.

The invention furthermore relates to pharmaceutical compositions which contain an effective amount of the compound of the formula I and a physiologically acceptable vehicle, as well as to a process for the preparation of these compositions, which comprises converting the active substance together with the vehicle and, where appropriate, further auxiliaries or additives into a suitable dosage form. The proportion of active substance in these compositions is, as a rule, 0.1 to 96%.

Intranasal, buccal, intravenous, subcutaneous or oral use is possible. The dosage of active substance depends on the warm-blooded species, the body weight, age and the mode of administration.

The pharmaceutical products of the present invention are prepared in dissolution, mixing, granulating or coating processes known per se.

For a form for oral use, the active compounds are mixed with the additives customary for this purpose, such as excipients, stabilizers or inert diluents, and converted by customary methods into suitable dosage forms such as tablets, coated tablets, hard gelatin capsules, aqueous, alcoholic or oily suspensions or aqueous, alcoholic or oily solutions. Examples of suitable inert vehicles are gum arabic, magnesium carbonate, potassium phosphate, lactose, glucose or starch, especially corn starch. In this connection, both dry and wet granules are possible for the composition. Examples of suitable oily excipients or solvents are vegetable or animal oils, such as sunflower oil or fish liver oil.

For subcutaneous or intravenous administration, the active compounds or the physiologically tolerated salts thereof are converted, if desired with substances customary for this purpose, such as solubilizers or other auxiliaries, into a solution, suspension or emulsion. Suitable for this purpose are, for example: water; physiological saline or alcohols, for example ethanol, propanol or glycerol, as well as sugar solutions such as glucose or mannitol solutions, or else a mixture of the various solvents mentioned.

The examples which follow serve to illustrate the present invention without intending to restrict the latter thereto.

List of abbreviations used:
AA: amino acid analysis
Ac: acetyl
Boc: tert.-butoxycarbonyl
TLC: thin-layer chromatography
DCC: dicylcohexylcarbodiimide
DCU: dicylcohexylurea
DMF: dimethylformamide
DMSO: dimethyl sulfoxide
EA: ethyl acetate
FAB: fast atom bombardment
Fmoc: 9-fluorenylmethyloxycarbonyl
HOBt: 1-hydroxybenzotriazole
HOSu: 1-hydroxysuccinimide
HPhe: homophenlalanine
M: molecular peak
MeOH: methanol
MS: mass spectrum
CHN: elemental analysis
NEM: N-ethylmorpholine
tBu: tert.butyl
Pht: phthalyl
m.p.: melting point
THF: tetrahydrofuran
Z: benzyloxycarbonyl
h: hour min: minute
RT: room temperature
Tic: 1,2,3,4-tetrahydroisoquinoline
Phg: phenylglycine The other abbreviations used for amino acids and protective groups correspond to the letter code customary in peptide chemistry, as is described, for example, in Europ. J. Biochem. 138, 9–37 (1984). Unless expressly indicated otherwise, the amino acids are always in the L configuration.

EXAMPLES

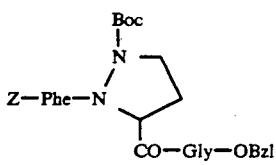
A.1.

A.1.1. Ethyl 1-tert.-butoxycarbonylpyrazolidinecarboxylate 53.5 g of Diazald ® in 750 ml of tert.-butyl methyl ether are cooled to 0° C., and 16.5 g of KOH dissolved in 250 ml of ethanol/water (9:1) are added. The mixture is warmed to room temperature and stirred at room temperature for 1 h. 25.0 g (0.25 mol) ethyl acrylate in 20 ml of tert.-butyl methyl ether are added dropwise over 1.5 h, with 40 ml of water being added towards the end. For the working up, 800 ml of diethyl ether are added, and the organic phase is separated off, washed with saturated NaCl solution and dried over Na$_2$SO$_4$. The residue is dissolved in 500 ml of DMF, and 55 ml of triethylamine, 100 mg of N,N-dimethylaminopyridine and 54 g (0.25 mol) of di-tert.-butyl pyrocarbonate are added. Chromatography on silica gel results in 8 g of ethyl Δ$_2$-1-tert.-butoxycarbonylpyrazoline-3-carboxylate. 6 g of the pyrazoline derivatives are dissolved in 100 ml of acetic acid, and 7 g of zinc powder are added and stirred. The reaction solution is removed by filtration after 2 h, the filtrate is evaporated in a rotary evaporator, and the residue is chromatographed on silica gel. 4.5 g of ethyl 1-tert.-butoxycarbonylpyrazolidine-3-carboxylate are obtained.

$^1$H NMR: δ (TMS)=1.3; 1.5; 2.0–2.5; 3.4–3.7; 3.9; 4.25 ppm
MS (FAB)=245 (M+H)

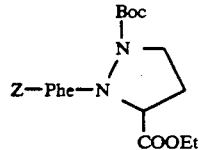
A.1.2.

598 mg of Z-Phe-OH in 5 ml of CH$_2$Cl$_2$ are cooled to 0° C. and a solution of 420 mg of DCC in 1 ml of CH$_2$Cl$_2$ is added, and the mixture is stirred at 0° C. for 30 minutes and then at room temperature for 30 minutes. The urea is removed by filtration, the filtrate is evaporated in vacuo, and the residue is chromatographed on silica gel. 610 mg of the target compound are obtained.

$^1$H NMR: δ (TMS)=1.35 and 1.5 ($^t$Bu), 4.2 (OCH$_2$) ppm
MS (FAB)=526 (M+H)

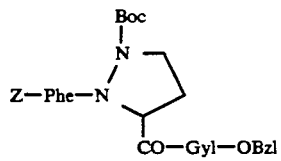
A.1.3.

600 mg of the dipeptide are hydrolyzed with 4N NaOH in dioxane/methanol, titrating with thymolphthalein. The pH is then adjusted to 2 with 1N HCl, the mixture is extracted with EA, and the organic phase is washed with saturated NaCl solution and dried over Na$_2$SO$_4$. The residue (550 mg) is dissolved with 343 mg of H-Gly-OBzl.toluenesulfonic acid in 3 ml of CH$_2$Cl$_2$, cooled to 0° C. and a solution of 230 mg of DCC in CH$_2$Cl$_2$ is added, with addition of 150 μl of NEM. The mixture is stirred at 0° C. for 15 minutes and at room temperature for 20 minutes, and the solvent is removed in a rotary evaporator. The diastereomers can be separated by chromatography on silica gel (ethyl acetate/petroleum ether 2:1). 150 mg of the pyrazolidine derivative with the R configuration, and the 130 mg of that with the S configuration, are obtained.

$^1$H NMR: δ (TMS)=1.35 ((R)-$^t$Bu), 1.15 ((S)-$^t$Bu) ppm.
MS (FAB)=645 (M+H)

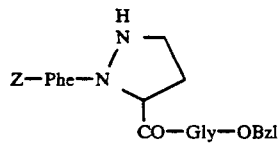
A.2.

120 mg of the Boc-protected pyrazolidine derivative from A.1.3. in 4 ml of 9N ethereal HCl solution are stirred at room temperature for 45 minutes. It is then evaporated in a rotary evaporator, again taken up in diethyl ether and evaporated in a rotary evaporator. 100 mg of the target compound are obtained as the hydrochloride.

MS (FAB=545 (M+H)

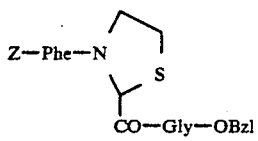
B.1.

B.1.1. Ethyl thiazolidine-2-carboxylate 22.6 g of mercaptoethylamine hydrochloride and 20.4 g of ethyl glyoxylate are heated with 100 g of 3A molecular sieves on a water bath for 45 min. The mixture is filtered, the filtrate is evaporated in vacuo, the residue is filtered through silica gel and the product is crystallized from methylene chloride/tert.-butyl methyl ether. 27 g of the thiazolidine derivative are obtained.

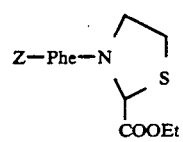
B.1.2.

1.98 g of ethyl thiazolidine-2-carboxylate, 2.99 g of Z-Phe-OH and 1.35 g of HOBt are dissolved in a little DMF and cooled to 0° C., and 2.1 g of DCC and 1.28 ml of NEM are successively added. The mixture is stirred at 0° C. for 1 h and at RT for a further 10 h. The urea is removed by filtration, the filtrate is evaporated in a rotary evaporator, the residue is taken up in ethyl acetate, and the solution is filtered through silica gel. 4 g of the target compound are obtained as an oil which is immediately processed further as in B.1.3.

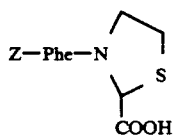

B.1.3.

4 g of the reaction product from B.1.2. are disclosed in 20 ml of dioxane and 5 ml of $H_2O$ and hydrolyzed with 1N NaOH solution, titrating with thymolphthalein. After the reaction is complete, checking by TLC, the mixture is acidified with $KHSO_4$ solution, and the aqueous phase is extracted with EA. The organic phase is washed with saturated NaCl solution and dried over $Na_2SO_4$. Evaporation in a rotary evaporator results in 3.6 g of the target compound as an oil.

MS (FAB)=415 (M+H)

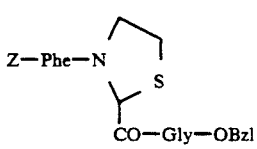

B.1.4.

3.4 g of the reaction product from B.1.3., 2.7 g of the toluenesulfonic acid salt of H-Gly-OBzl and 1.1 g of HOBt are dissolved in 8 ml of DMF and cooled to 0° C., and 1.7 g of DCC and 1.1 ml of NEM are added. The mixture is stirred at 0° C. for 1 h and at RT for a further 10 h. The urea is removed by filtration, the solution is evaporated in a rotary evaporator, the residue is taken up in EA, the solution is washed with $KHSO_4$ solution, with $KHCO_3$ solution and with NaCl solution and dried over $Na_2SO_4$, and the solvent is removed in a rotary evaporator. The crude product is purified by chromatography on silica gel (diethyl ether). 4 g of the target compound are obtained.

$^1$H NMR: δ (TMS)=2.8–3.2; 3.6–5.6; 7.0–7.6 ppm
MS (FAB)=562 (M+H)

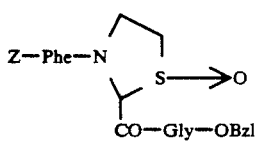

B.2.

1.4 g of the tripeptide from B.1.4. are dissolved in 5 ml of methanol, and 0.35 ml of 30% strength $H_2O_2$ solution is added. The mixture is stirred at RT for 20 h and evaporated almost to dryness in vacuo, the and residue is chromatographed on silica gel ($CH_2Cl_2/CH_3OH$:25/2). 150 mg (I) and 200 mg (II) of the sulfoxides are isolated as diastereomers.

I: $^1$H NMR: δ (TMS=2.9–3.2; 3.5; 3.85; 4.1; 4.35; 4.6; 5.0–5.2; 5.45; 7.1–7.5. ppm MS (FAB)=578 (M+H)
II: $^1$H NMR: δ (TMS)=2.8–3.2; 7.1–7.4 ppm
MS (FAB)=578 (M+H)

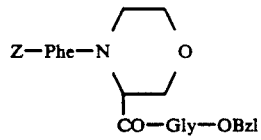

C.1.

C.1.1. Ethyl morpholine-2-carboxylate

Synthesis by the method of Y. Kogami, K. Okawa, Pept. Chemistry 1985, 153–156.

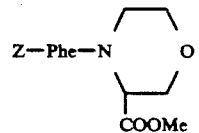

C.1.2.

533 mg of methyl morpholine-2-carboxylate and 1090 mg of Z-Phe-OH are dissolved together in 10 ml of $CH_2Cl_2$, the solution is cooled to 0° C., and 760 mg of DC and 0.45 ml of NEM are added. The mixture is stirred at RT for 5 h, the urea is removed by filtration, and the solvent is removed by evaporation in vacuo. The residue is taken up in EA and purified by chromatography on silica gel (diethyl ether). 600 mg of the target compound are obtained.

MS (FAB)=427 (M+H)
$^1$H NMR: δ (TMS)=3.65 and 3.8 ($OCH_3$) ppm.

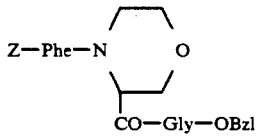

C.1.3.

600 mg of the reaction product from C.1.2. are hydrolyzed under the conditions of B.1.3. 430 mg of the acid are obtained and are dissolved with 352 mg of the p-toluenesulfonic acid salt of H-Gly-OBzl in 5 ml of DMF and 5 ml of $CH_2Cl_2$. The solution is cooled to 0° C., and 215 mg of DCC and 0.13 ml of NEM are added. The mixture is warmed to RT and stirred for 2 h. After DCU has been filtered off and the solvent has been removed by evaporation in vacuo, the residue is purified by chromatography on silica gel (EA/n-hexane: 2/1). 400 mg of the target compound are obtained.

$^1$H NMR: δ (TMS)=2.1; 3.0–3.2; 3.4; 3.65; 4.9–5.2; 5.45; 7.1–7.5 ppm.
MS (FAB)−560 (M+H)

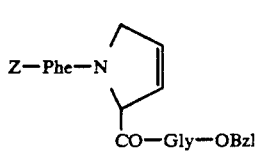

D.1.

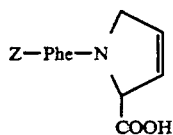

50 mg of L-3,4-dihydroproline are dissolved in 0.44 ml of 1N NaOH, and 175 mg of Z-Phe-OSu in 2 ml of ethanol are added. The mixture is stirred at RT for 2 h, continuously adjusting to pH=9. Aqueous HCl solution is subsequently used to adjust to pH=2, and the mixture is extracted with EA. Drying of the organic phase with NA$_2$SO$_4$ and evaporation of the solvent in vacuo results in the target compound as a crude product which is immediately reacted further as in D.1.2.

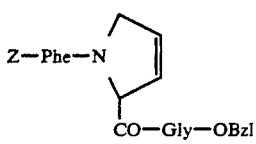

The crude product from D.1.1. is dissolved in 150 mg of the p-toluenesulfonic acid salt of H-Gly-OBzl and 60 mg of HOBt in 5 ml of CH$_2$Cl$_2$, the solution is cooled to 0° C., and 91 mg of DCC and 56 μl of NEM are added. The mixture is stirred at 0° C. for 1 h at RT for 2 h. The DCU is filtered off and then the solvent is evaporated in vacuo and the residue is chromatographed on silica gel. 40 mg of the target compound are obtained.

$^1$H NMR: δ (TMS)=3.05 (CH$_2$—Phe); 5.1 and 5.2 (CH$_2$—OCO) ppm.

MS (FAB)=542 (M+H)

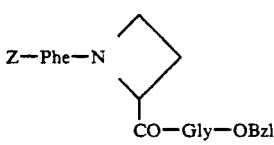

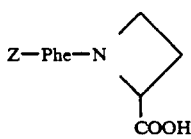

500 mg of L-azetidine-2-carboxylic acid are dissolved in 4.9 ml of 1N NaOH. 4 ml of ethanol and 1.96 g of Z-Phe-OSu are added, and the mixture is stirred at RT for 2 r. KHSO$_4$ solution is then used to adjust to pH=2, and the mixture is extracted several times with EA. After drying over Na$_2$SO$_4$, the residue is reacted further as in E.1.2.

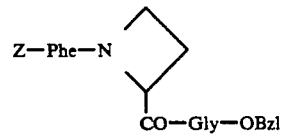

The crude product from E.1.1. is dissolved with 1.68 g of the p-toluenesulfonic acid salt of H-Gly-OBzl, 675 mg of HOBt, 1.03 g of DCC and 0.64 ml of NEM in 15 ml of CH$_2$Cl$_2$, and the mixture is stirred at RT for 4 h. Removing the urea by filtration, evaporation in vacuo an crystallization of the residue from diethyl ether provide 1.8 g of the tripeptide.

NMR: 2.3-2.5; 2.8-3.0; 3.3; 4.1; 4.4; 4.85; 5.1; 5.2; 5.5; 7.1-7.5 ppm

MS (FAB): 530 (M+H)

We claim:

1. A compound of the formula $$A-Cyc-NH-CH(R^8)-C(=O)-O-R^4 \quad (I)$$

in which

A denotes (C$_1$-C$_8$)-alkoxycarbonyl, in which one hydrogen atom is optionally replaced by (C$_6$-C$_{12}$)-aryl, or A denotes a radical of the formula IIa $$R^1-N(R^2)-CH(R^3)-C(=O)- \quad (IIa)$$

in which

R$^1$ denotes (C$_6$-C$_{12}$)-aryl-(C$_1$-C$_4$)-alkoxycarbonyl;

R$^2$ denotes hydrogen;

R$^3$ denotes (C$_1$-C$_4$)-alkyl which is monosubstituted by phenyl; and

Cyc denotes

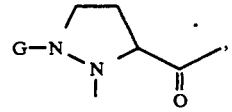

wherein G denotes hydrogen;

R$^4$ denotes (C$_6$-C$_{12}$)-aryl-(C$_1$-C$_5$)-alkyl; and

R$^8$ is hydrogen, as well as the salts thereof.

2. A compound of the formula I as claimed in claim 1, in which A denotes benzyloxycarbonyl or a radical of the formula IIa, wherein R$^1$ denotes benzyloxycarbonyl, R$^2$ denotes hydrogen, and R$^3$ and R$^4$ denote benzyl.

3. A method for the in vitro inhibition of prolyl hydroxylase, which comprises administering an effective amount of a compound of the formula I as claimed in claim 1.

* * * * *

UNITED STATES PATENT AND TRADEMARK OFFICE
CERTIFICATE OF CORRECTION

PATENT NO. : 5,206,343
DATED : April 27, 1993
INVENTOR(S) : Stephan Henke et al.

It is certified that error appears in the above-indentified patent and that said Letters Patent is hereby corrected as shown below:

TITLE PAGE

Item [75], change "Gunzlen" to --Gunzler--.

Foreign Application Priority Data, insert --June 3, 1988 [DE] Fed. Rep. of Germany.....3818850--.

Claim 3, column 16, line 57, italicize "in vitro".

Signed and Sealed this

Twenty-first Day of June, 1994

Attest:

BRUCE LEHMAN

Attesting Officer  Commissioner of Patents and Trademarks